US012766033B2

(12) United States Patent
Kocher et al.

(10) Patent No.: US 12,766,033 B2
(45) Date of Patent: Oct. 20, 2026

(54) PHACOEMULSIFICATION HANDPIECE

(71) Applicant: Bausch + Lomb Ireland Limited, Dublin (IE)

(72) Inventors: Christopher Kocher, St. Louis, MO (US); Jason Taylor, Ballwin, MO (US); Elijah Kessler, St. Louis, MO (US)

(73) Assignee: Bausch + Lomb Ireland Limited, Dublin (IE)

( * ) Notice: Subject to any disclaimer, the term of this patent is extended or adjusted under 35 U.S.C. 154(b) by 892 days.

(21) Appl. No.: 17/365,353

(22) Filed: Jul. 1, 2021

(65) Prior Publication Data

US 2023/0000679 A1 Jan. 5, 2023

(51) Int. Cl.
*A61F 9/007* (2006.01)
*A61B 17/32* (2006.01)

(52) U.S. Cl.
CPC .................... *A61F 9/00745* (2013.01); *A61B 2017/320084* (2013.01); *A61B 2217/007* (2013.01)

(58) Field of Classification Search
CPC ..... A61F 9/00745; A61B 2017/320084; A61B 2217/007
See application file for complete search history.

(56) References Cited

U.S. PATENT DOCUMENTS

| | | | | |
|---|---|---|---|---|
| 4,681,561 | A | 7/1987 | Hood et al. | |
| 5,038,756 | A | 8/1991 | Kepley | |
| 5,413,556 | A | 5/1995 | Whittingham | |
| 5,486,162 | A | 1/1996 | Brumbach | |
| 5,685,838 | A * | 11/1997 | Peters | A61B 17/32002 606/171 |
| 2001/0018570 | A1* | 8/2001 | Sussman | A61M 1/77 604/114 |
| 2001/0027601 | A1* | 10/2001 | Stoddard | A61F 9/00745 29/527.2 |
| 2010/0160852 | A1* | 6/2010 | Moore, Jr. | A61F 9/00745 604/22 |
| 2015/0025451 | A1* | 1/2015 | Banko | A61M 1/774 604/35 |
| 2018/0200109 | A1* | 7/2018 | Chon | A61M 1/774 |

* cited by examiner

*Primary Examiner* — Andrew Restaino
(74) *Attorney, Agent, or Firm* — Harness, Dickey & Pierce, P.L.C.

(57) ABSTRACT

A phacoemulsification handpiece is provided for ophthalmic surgery. The phacoemulsification handpiece includes a housing having a cavity positioned at a distal end of the housing. The phacoemulsification handpiece further includes a horn positioned within the cavity. An irrigation line is coupled to the housing and is exterior to the housing. A port is coupled between the irrigation line and the cavity and the port is configured to direct fluid into the cavity to a side of the horn (e.g., without directly impinging on the horn, etc.).

5 Claims, 13 Drawing Sheets

PHACOEMULSIFICATION HANDPIECE

FIELD

The present disclosure generally relates to phacoemulsification handpieces and related systems, and more particularly, to phacoemulsification handpieces having offset irrigation ports.

BACKGROUND

This section provides background information related to the present disclosure which is not necessarily prior art.

Ophthalmic surgery often involves cutting away or emulsifying tissues that need to be removed from the eye, such as in cataract surgery. One known technique is phacoemulsification. This technique involves using high frequency ultrasound energy transmitted through a handpiece into a phacoemulsification needle to emulsify the affected tissue. To maintain the eye in a pressurized condition during surgery and to aid in the aspiration of the affected tissue, a saline fluid is introduced into the eye through the handpiece. Prior to surgery, the saline fluid is passed through the handpiece in a process known as priming. As the saline fluid flows through the handpiece during priming, air bubbles within the handpiece are evacuated. However, priming may not always remove all of the air from the handpiece (e.g., when the handpiece is not oriented correctly during priming, etc.) and this remaining air may cause problems if subsequently transmitted into the eye during surgery. For example, air bubbles in the saline fluid can cause visualization problems for the surgeon, can cause damage to corneal endothelial cells, and may cause an unwanted change in intra-ocular pressure.

SUMMARY

This section provides a general summary of the disclosure, and is not a comprehensive disclosure of its full scope or all of its features.

Example embodiments of the present disclosure generally relate to phacoemulsification handpieces for ophthalmic surgery. In one example embodiment, a phacoemulsification handpiece generally includes a housing having a cavity positioned at a distal end of the housing. The housing includes a central longitudinal axis. The phacoemulsification handpiece further includes a horn positioned within the cavity, wherein the horn is coaxial with the central longitudinal axis. An irrigation line is coupled to the housing and may be exterior to the housing. A port is coupled between the irrigation line and the cavity, and the port is configured to direct fluid into the cavity to the side of the horn (e.g., without directly impinging on the horn, etc.) with respect to the central longitudinal axis. In some embodiments, the irrigation line and the port are laterally offset with respect to the central longitudinal axis, so as to direct fluid to the side of the horn. In some embodiments, the port is angled such that fluid is directed by the port away from the horn and to the side of the horn.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1A:
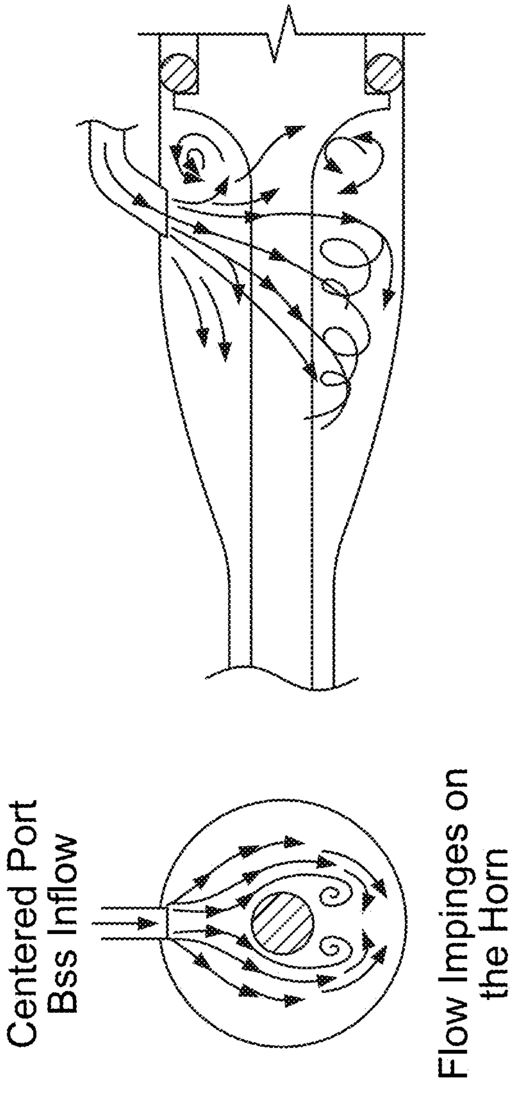
FIG. 1A (Prior Art)
FIG. 1A is a flow diagram including notional streamlines of fluid in an existing phacoemulsification handpiece.
Figure 1B:
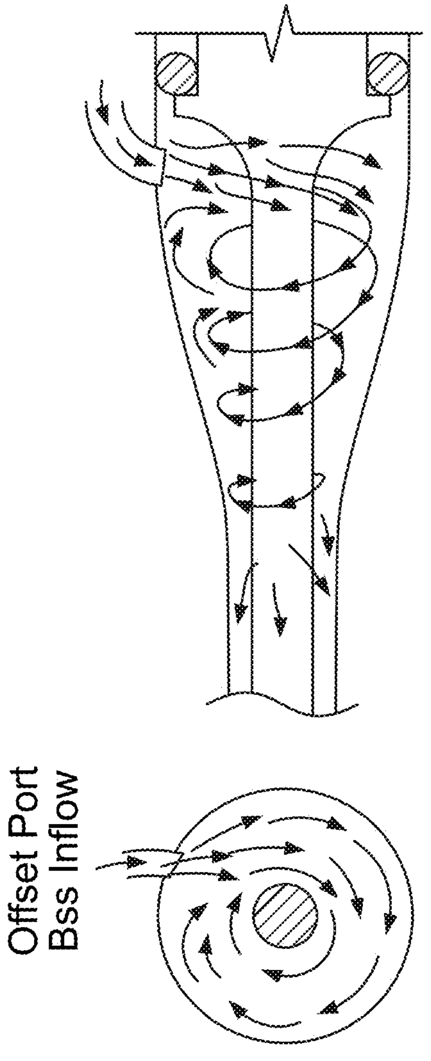
FIG. 1B is a flow diagram including notional streamlines of fluid in an example embodiment of a phacoemulsification handpiece.
Figure 2:
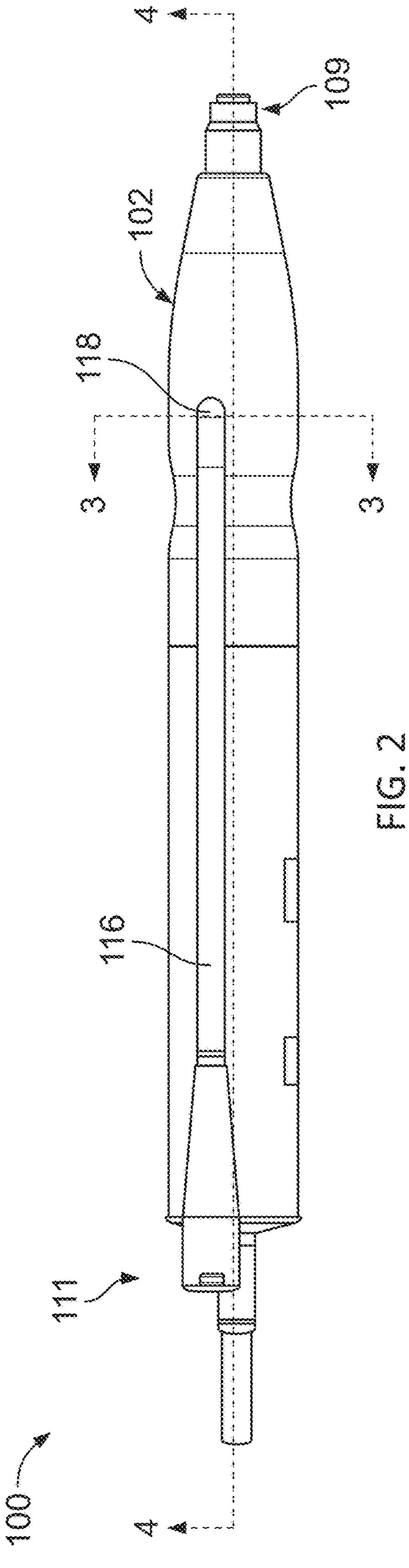
FIG. 2 is a top view of an example embodiment of a phacoemulsification handpiece.
Figure 3B:
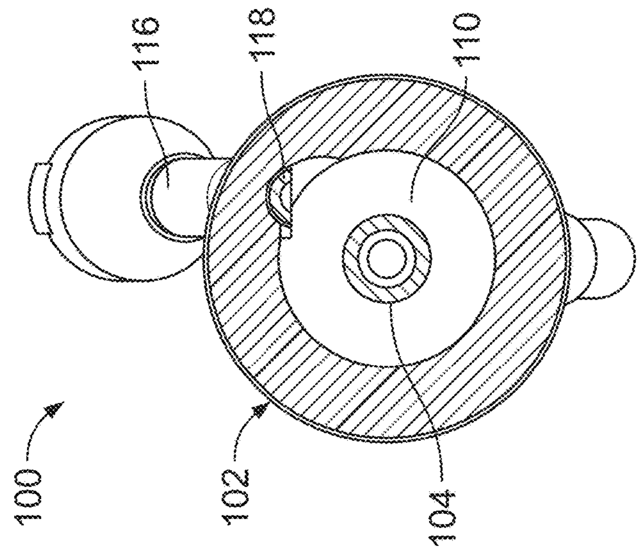
FIG. 3B is a cross-section view of the phacoemulsification handpiece of FIG. 2 taken along line 3-3 in order to illustrate an irrigation port of the phacoemulsification handpiece (e.g., laterally offset from a central longitudinal axis of the handpiece, etc.)
Figure 3A:
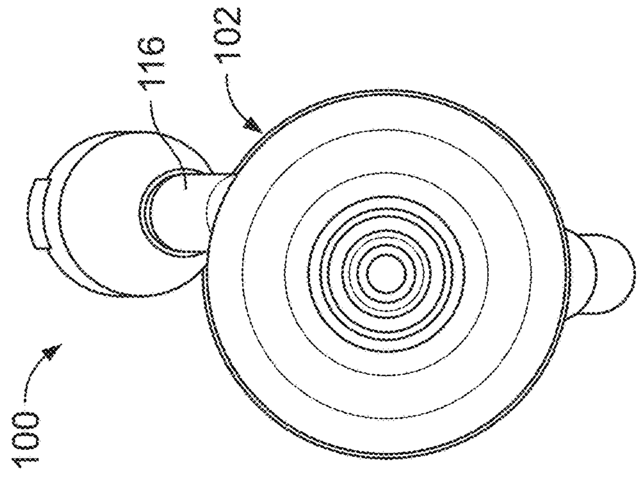
FIG. 3A is a front elevation view of the distal end of the phacoemulsification handpiece of FIG. 2.
Figure 4:
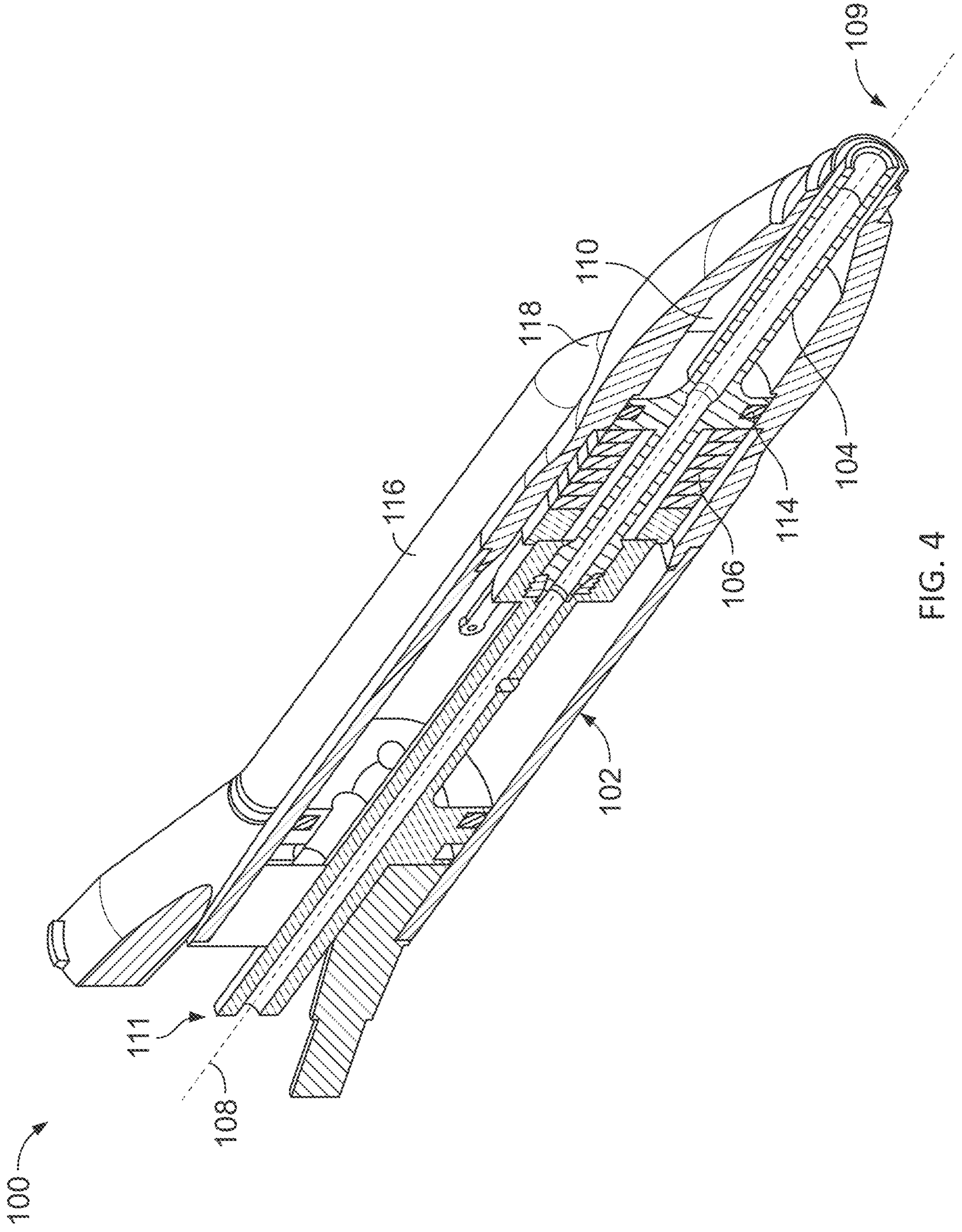
FIG. 4 is a cross-sectional perspective view of the phacoemulsification handpiece of FIG. 2 taken along line 4-4.

Example embodiments of the present disclosure generally relate to phacoemulsification handpieces for ophthalmic surgery. Current phacoemulsification handpieces introduce a balanced salt solution ("BSS") into the handpiece through a port that is oriented such that the BSS impinges directly on an ultrasonic horn included within handpiece. The direct impingement results in vortices/eddies within the flow of the BSS through the handpiece, as shown in FIG. 1A, which are inefficient at removing air from the handpiece during priming and may create additional air bubbles within the handpiece. Uniquely, the phacoemulsification handpieces of the present disclosure modify the positioning and orientation of the ports such that the BSS is introduced into the handpiece without direct impingement on the horn (e.g., to the side of the horn, approximately tangent to the inner wall of the handpiece, etc.), as shown in FIG. 1B. This creates an efficient and less turbulent fluid flow of the BSS within the housing. The resulting fluid flow more efficiently removes air from the housing during priming and minimizes the creation of air bubbles, which decreases the likelihood that trapped air would subsequently enter the eye during surgery.

Example embodiments will now be described more fully with reference to the accompanying drawings. The description and specific examples included herein are intended for purposes of illustration only and are not intended to limit the scope of the present disclosure.

FIGS. 2-5 illustrate an example embodiment of a phacoemulsification handpiece 100 (broadly, a handpiece) including one or more aspects of the present disclosure. In the illustrated embodiment, the handpiece 100 generally includes a housing 102 and a horn 104 positioned within the housing 102. The horn 104 (e.g., an ultrasonic transducer horn) is coupled to a plurality of transducers 106 (e.g., a piezo-electric vibration stack) which are configured to ultrasonically vibrate the horn (and an unshown needle attached thereto) during surgery to emulsify affected tissue. As shown, the horn 104 is aligned (e.g., coaxial) with a central longitudinal axis 108 of the handpiece 100, the central longitudinal axis 108 extending from a distal end 109 of the handpiece 100 through a proximal end 111 of the handpiece 100. It is also noted that handpiece 100 and horn 104 may not be axially symmetric, such as in designs intended to create other than longitudinal vibration.

The horn 104 is positioned within a cavity 110 of the housing 102. The cavity 110 is located at the distal end 109 of the housing 102. The cavity 110 is defined, in part, by an inner wall 112 of the housing 102. In the illustrated embodiment, the diameter of the cavity 110 is larger at the proximal end of the cavity 110 than the diameter of the cavity 110 at the distal end of the cavity 110. As shown, the inner wall 112 may define a smooth transition between the larger diameter at the proximal end of the cavity 110 to the smaller diameter at the distal end of the cavity 110 (e.g., does not include stepped reductions in diameter). However, in other embodiments, the inner wall 112 may include other geometries, such as those including stepped reductions in diameter. Additionally, to protect the transducers 106 and other electronics included in the housing 102 of the handpiece 100, the handpiece 100 also includes a seal 114 (e.g., an o-ring) positioned around the horn 104 (e.g., at a base of the horn 104) to fluidly seal the transducers 106 and other electronics from fluid that may be present in the cavity 110 (e.g., during priming, during surgery, etc.).

Figure 5:
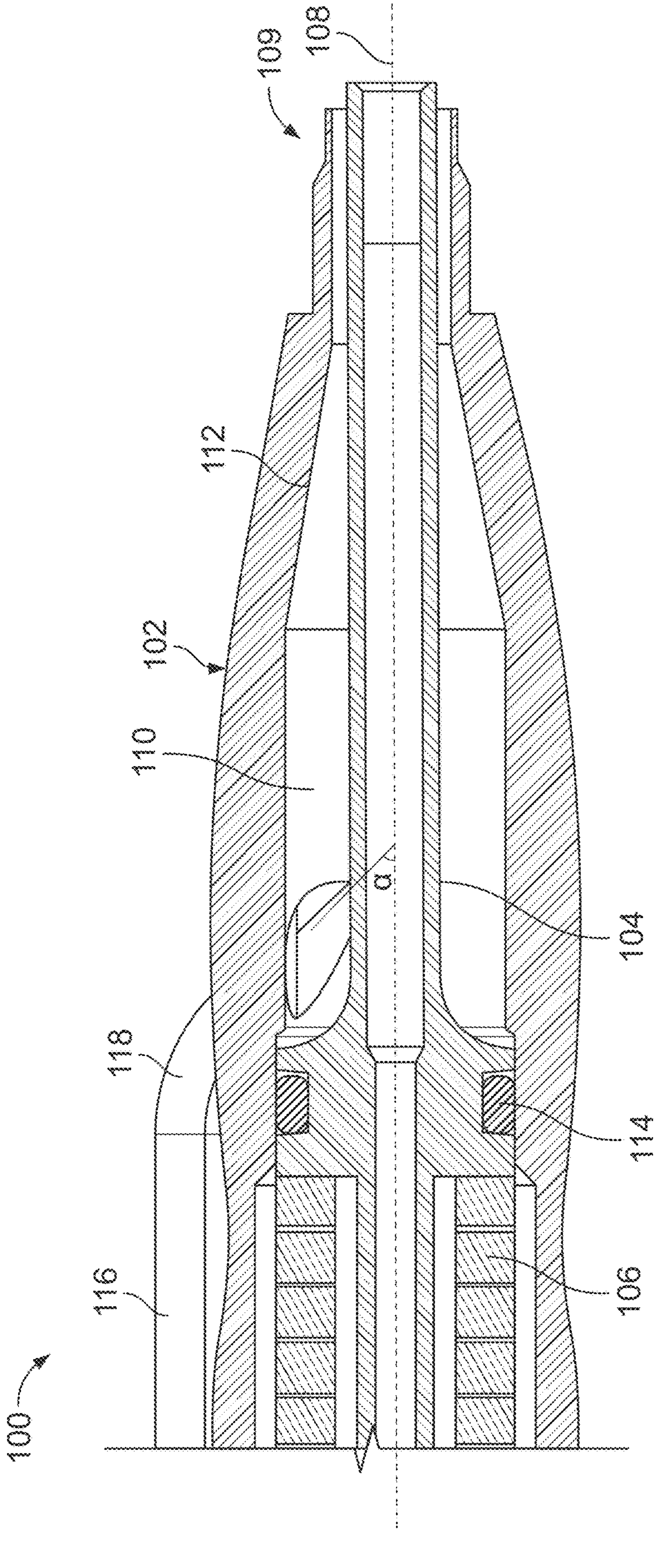
FIG. 5 is a partial side elevation view of the phacoemulsification handpiece of FIG. 2 taken along line 4-4.
Figure 6:
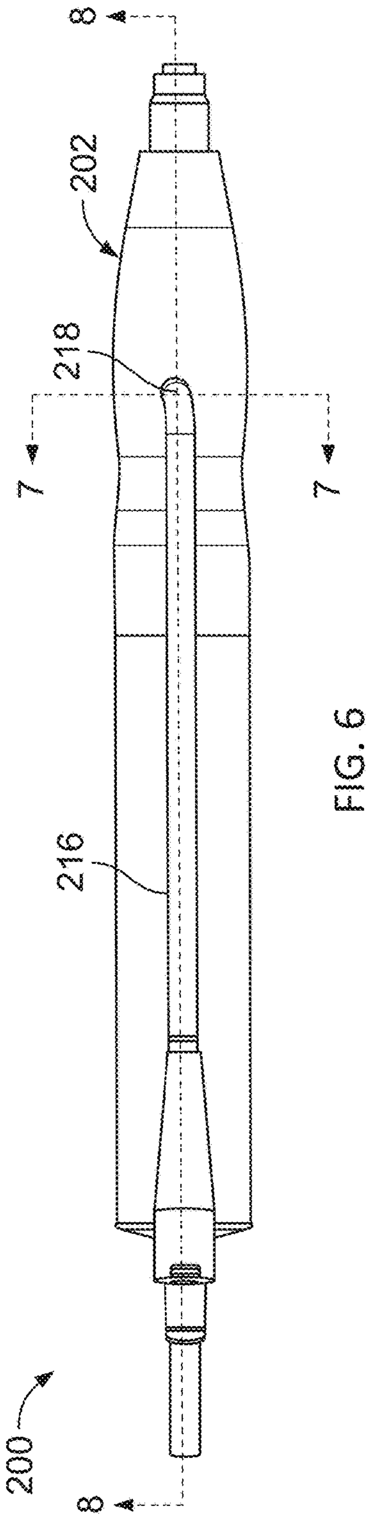
FIG. 6 is a top view of another example embodiment of a phacoemulsification handpiece.
Figure 15B:
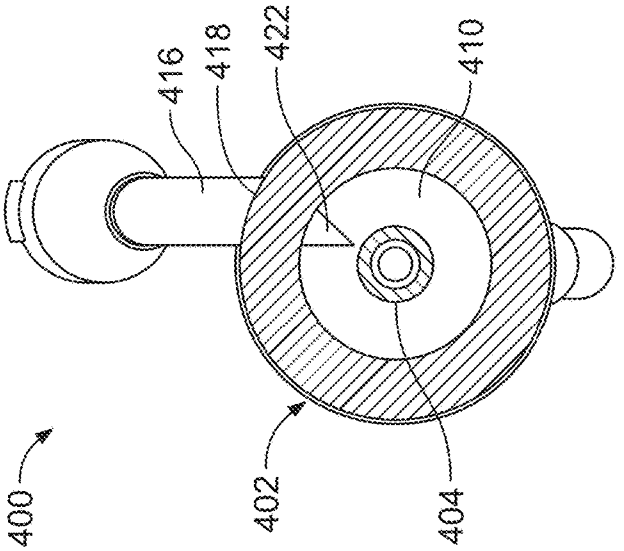
FIG. 15B is a cross-section view of the phacoemulsification handpiece of FIG. 14 taken along line 15-15 in order to illustrate an irrigation port of the phacoemulsification handpiece (e.g., laterally offset from a central axis of the handpiece, etc.)
Figure 15A:
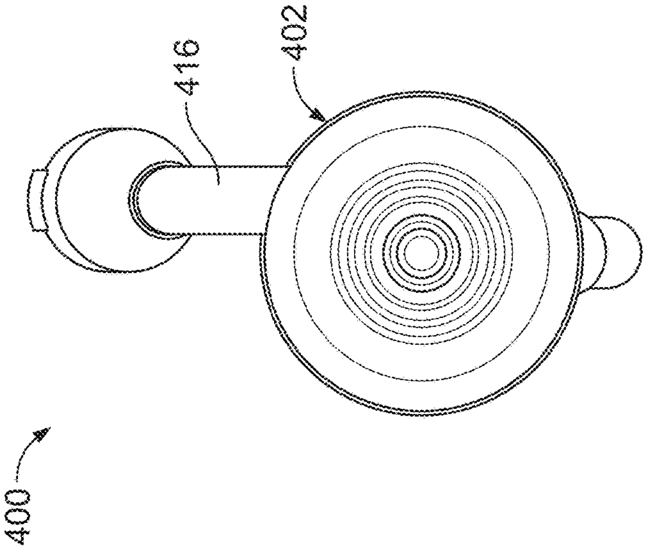
FIG. 15A is a front elevation view of the distal end of the phacoemulsification handpiece of FIG. 14.
Figure 16:
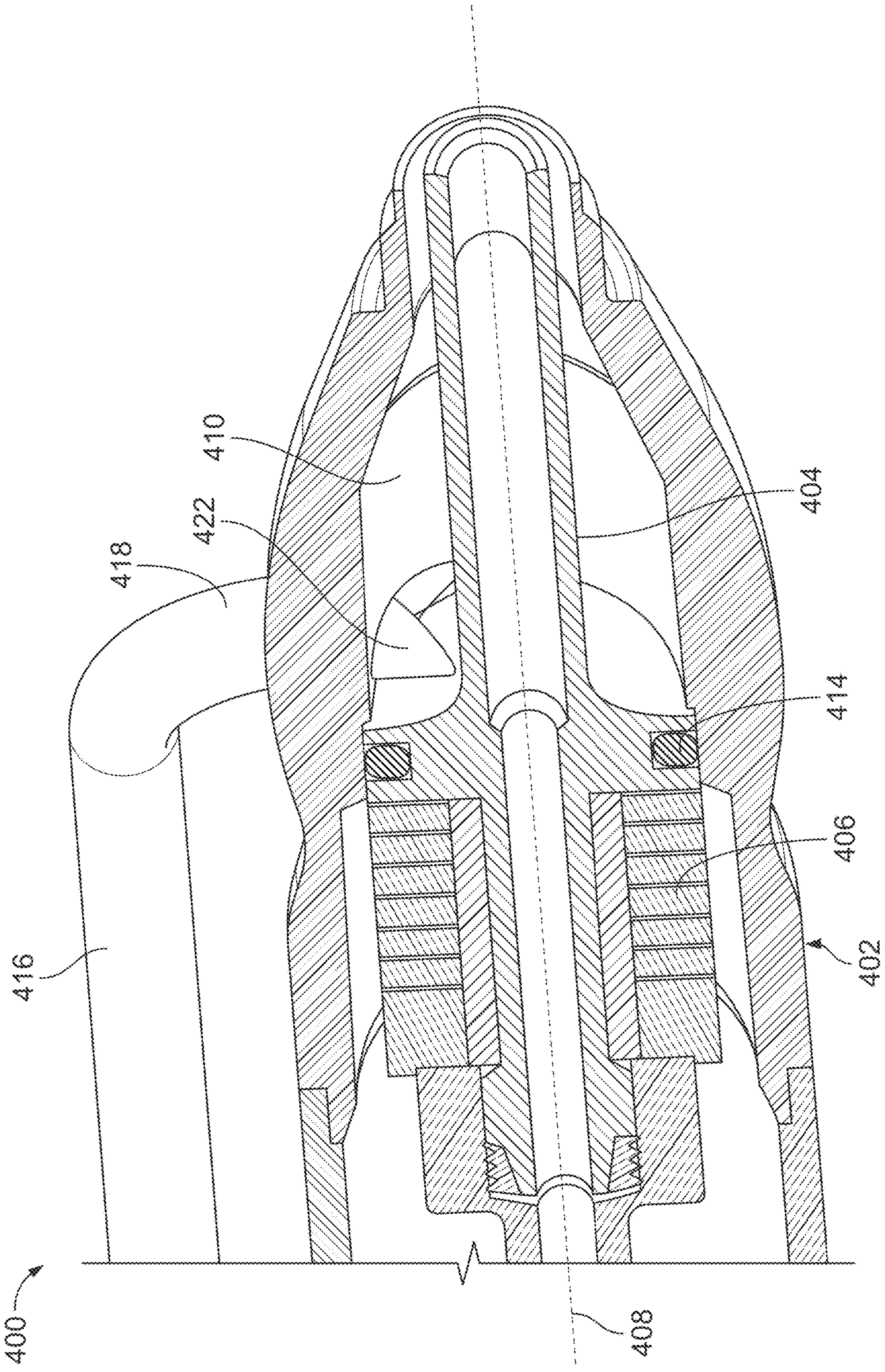
FIG. 16 is a partial side perspective view of the phacoemulsification handpiece of FIG. 14 taken along line 16-16.
Figure 17:
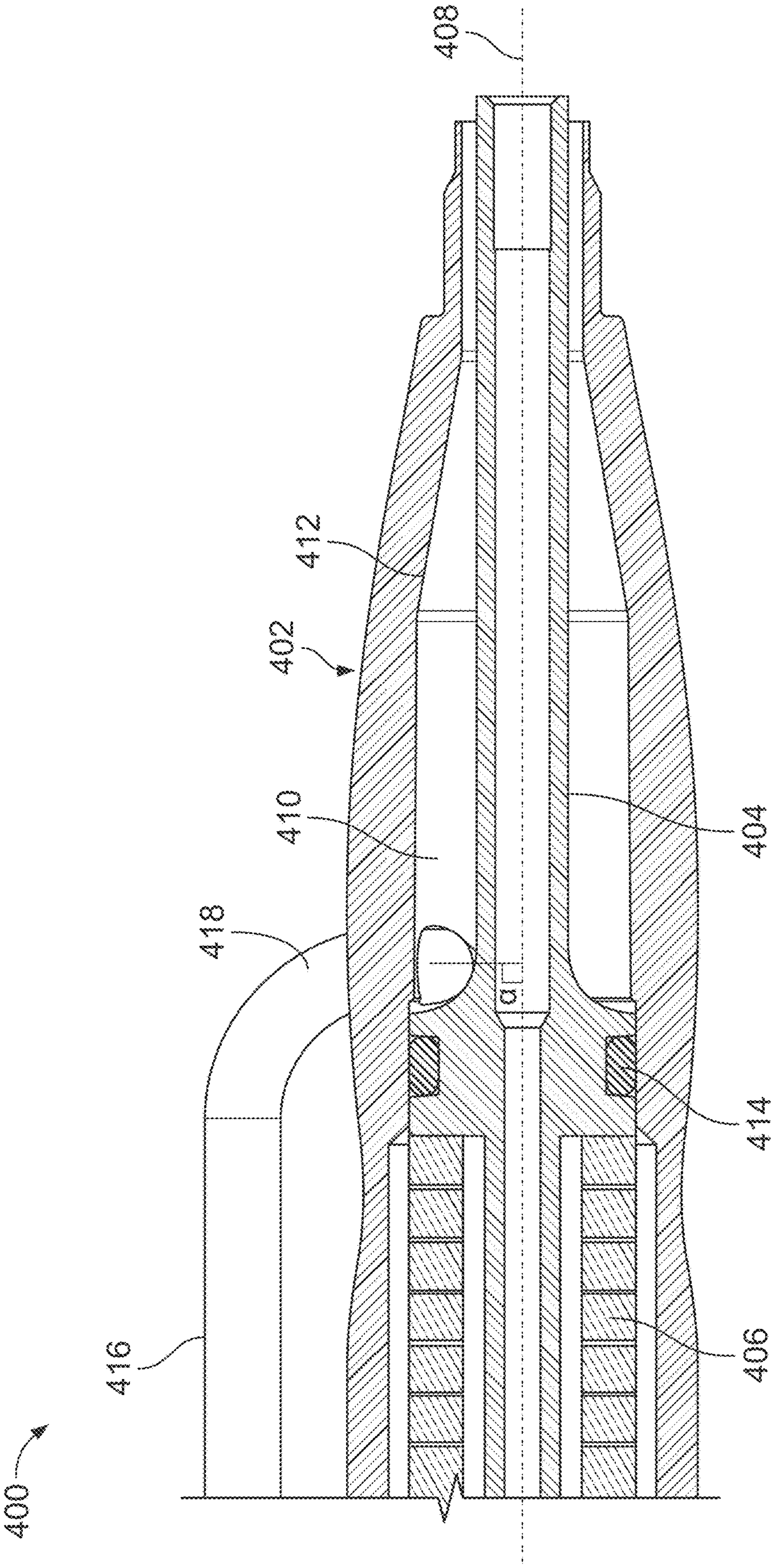
FIG. 17 is a partial side elevation view of the phacoemulsification handpiece of FIG. 14 taken along line 16-16.

The handpiece 100 also includes an irrigation line 116 that may be positioned external to the housing 102, as shown, or may be found within housing 102. Although not shown, the irrigation line 116 is coupled to a supply (e.g., a bag, a bottle, etc.) of irrigation fluid (e.g., a saline fluid, BSS, etc.). The irrigation fluid is directed into the cavity 110 from the irrigation line 116 via a port 118, where the port 118 is located towards the proximal end of the cavity 110. As shown, the inner wall 112 of the cavity 110 is parallel to the central longitudinal axis 108 at the location of the port 118 (e.g., at the proximal end of the cavity 110). In the illustrated embodiment, the port 118 does not extend into the cavity 110 (e.g., the end of the port 118 is aligned with the inner wall 112 of the housing 102). In other embodiments, the port 118 may extend at least partially into the cavity 110 (e.g., the port 118 includes a chamfered end which partially extends into the cavity to direct the irrigation fluid into the cavity 110, etc.) (see, e.g., FIG. 15B). As shown in FIG. 5, the port 118 is angled with respect to the central longitudinal axis 108 such that the irrigation fluid is directed into the cavity 110 at an infusion angle $\alpha$ (i.e., the angle at which the irrigation fluid enters the cavity with respect to the central axis 108). In the illustrated embodiment, for example, the infusion angle $\alpha$ of the port 118 is about forty-five degrees. However, in other embodiments, the infusion angle $\alpha$ may be greater or lesser (e.g., 30 degrees, 90 degrees, etc.), to optimize the flow of the irrigation fluid into and/or through the cavity 110. In some respects, depending on the design, port 118 may be considered the distal end of irrigation line 116, a passage formed through housing 102 into cavity 110, or a combination of both. An intention of the design is to have the irrigation fluid flow tangential to the inner wall 112 to create a swirling, non-turbulent flow.

In the illustrated embodiment, the irrigation line 116 and the port 118 are offset from the axis 108 (e.g., are not centered on the handpiece 100). In particular, the irrigation line 116 and the port 118 are shifted laterally from the axis 108 (e.g., laterally offset from the horn 104). The positioning of the offset port 118 both laterally and longitudinally may be selected in combination with the design of the cavity 110 to provide optimal, smooth fluid flow. In this way, when the irrigation fluid flows through the handpiece 100 (e.g., into the cavity 110), the irrigation fluid does not directly impinge the horn 104. Instead, the port 118 directs the irrigation fluid into the cavity 110 to the side of the horn 104 (e.g., lateral to the horn 104). In this way, the flow of the irrigation fluid generally revolves around the horn 104 (e.g., in a vortex-like flow) as the irrigation fluid flows through the cavity 110 (similar to the flow depicted in FIG. 1B). In other embodiments, the irrigation line 116 and the port 118 may be centered on the handpiece 100 (e.g., not laterally offset), but nonetheless direct the irrigation fluid into the cavity to the side of the horn 104, for example, by angling the port 114 away from the horn 104 (e.g., at an offset angle) (see FIGS. 7A-7B).

FIGS. 6-9 illustrate another example embodiment of a phacoemulsification handpiece 200 including one or more aspects of the present disclosure. The handpiece 200 of this embodiment is substantially similar to the handpiece 100 previously described and illustrated in FIGS. 2-5. For example, the handpiece 200 includes a housing 202 and a horn 204 (e.g., an ultrasonic transducer horn) that is positioned within a cavity 210 of the housing 202 and is coaxial with a central longitudinal axis 208 of the handpiece 200. The cavity 210 is positioned at a distal end of the housing 202 and is defined, in part, by an inner wall 212 of the housing 202 The handpiece 200 also includes an irrigation line 216 that is coupled to a supply of irrigation fluid (e.g., a saline fluid, BSS, etc.) and a port 218 coupled between the irrigation line 216 and the cavity 210.

In this embodiment, both the irrigation line 216 and the port 218 are axially aligned (e.g., coaxial) with the central longitudinal axis 208 of the handpiece 200. As such, rather than laterally offsetting the irrigation line 216 and the port 218 from the central longitudinal axis 208, the irrigation line 216 and the port 218 are coaxial with the axis 208, and the port 218 is instead angled (e.g., laterally angled) by offset angle β (shown in FIG. 7B), such that the irrigation fluid is directed into the cavity 210 to the side of the horn 204 (and generally tangent to the inner wall 212 of the housing 202). Angling the port 218 creates a flow of irrigation fluid through the cavity 208 that is similar to the flow created by offsetting the port (e.g., offset port 118). For example, the flow of the irrigation fluid generally revolves around the horn 204 (e.g., in a vortex-like flow) as the irrigation fluid flows through the cavity 210 (similar to the flow depicted in FIG. 1B), whereby trapped air is more reliably removed from the cavity 210 during priming of the handpiece 200. In particular, the flow provided by the angled port 218 does not directly impinge on the horn 204, resulting in a less turbulent flow, which creates fewer air bubbles. Moreover, centrally locating the irrigation line 216 and the port 218 (e.g., axially aligned with the axis 208, not laterally offset, etc.) may also result in a more ergonomic grip for a user of the handpiece 200. In some embodiments, the port may be angled at an offset angle β (e.g., similar to port 218) and is also laterally offset from the horn (e.g., similar to port 118). In such embodiments, the irrigation line may also be laterally offset from the horn and central longitudinal axis (e.g., similar to irrigation line 116).

Figure 7B:
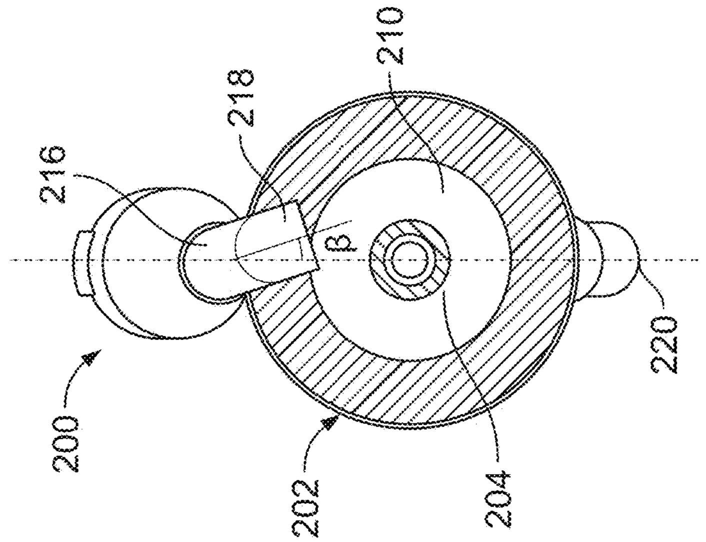
FIG. 7B is a cross-section view of the phacoemulsification handpiece of FIG. 6 taken along line 7-7 in order to illustrate an irrigation port of the phacoemulsification handpiece (e.g., at an offset angle from a central vertical axis of the handpiece, etc.)
Figure 7A:
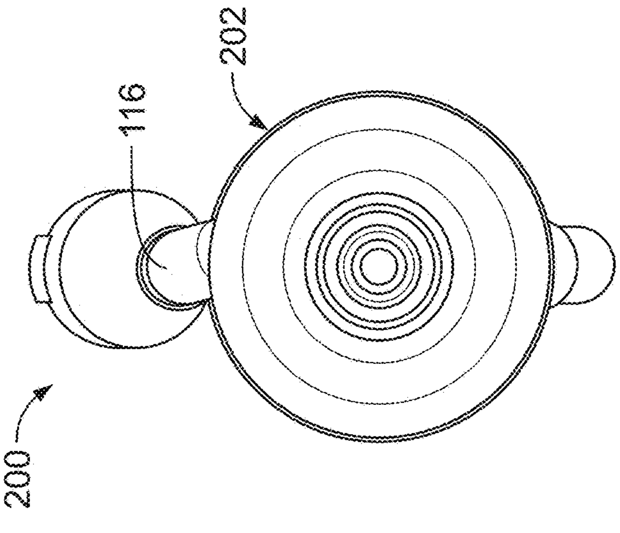
FIG. 7A is a front elevation view of the distal end of the phacoemulsification handpiece of FIG. 6.
Figure 8:
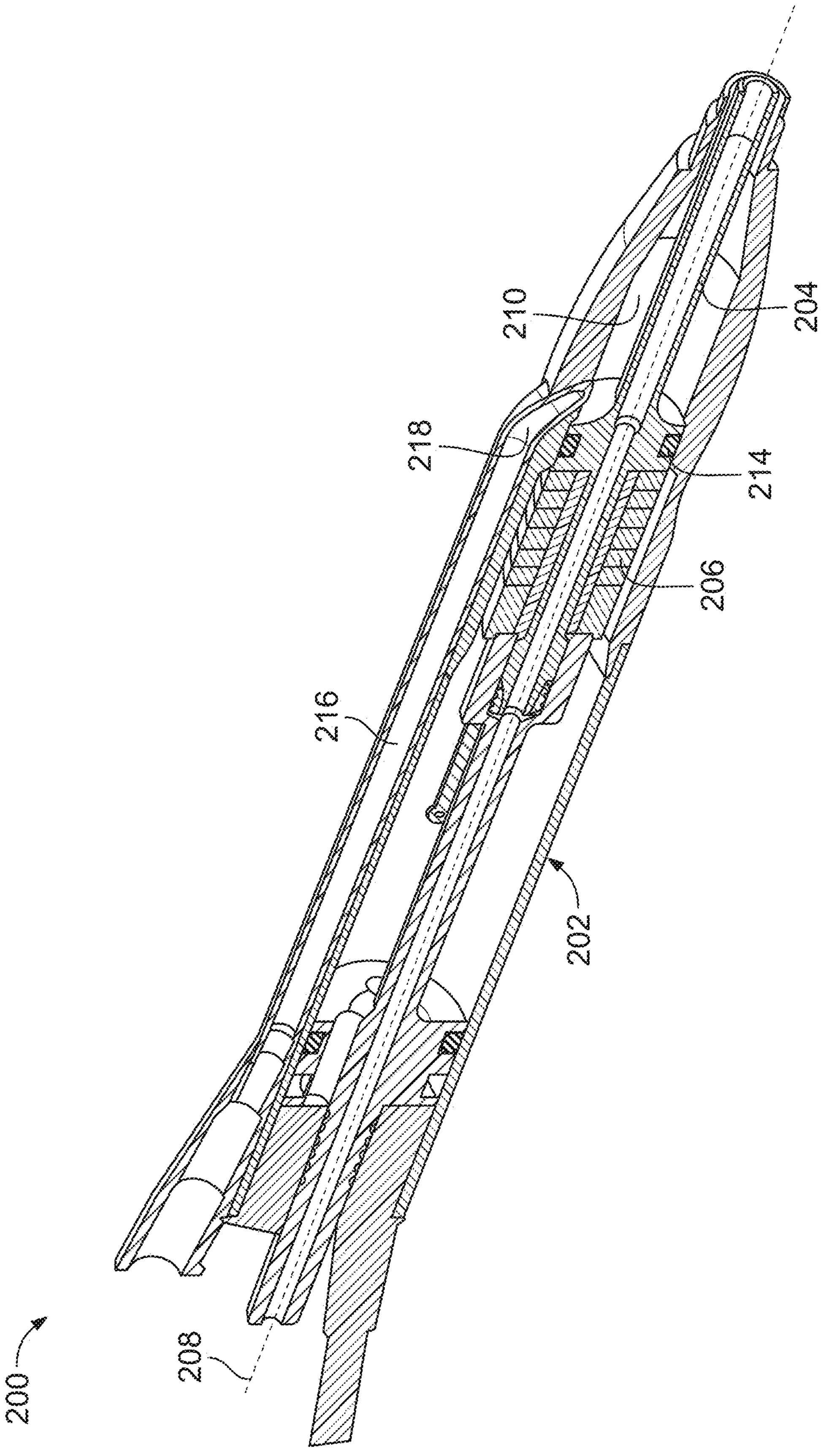
FIG. 8 is a cross-sectional perspective view of the phacoemulsification handpiece of FIG. 6 taken along line 8-8.

As shown in FIG. 7B, the port 218 is angled with respect to a vertical axis 220 of the handpiece 200 such that the irrigation fluid is directed into the cavity 210 at an offset angle (3 (i.e., the angle at which the irrigation fluid enters the cavity with respect to the vertical axis 220). The optimum offset angle will depend on the cavity geometry. It is also noted that the offset can be either to either side of the cavity and is not limited to the examples shown. The vertical axis 220 is perpendicular to the central longitudinal axis 208 (See FIG. 9) and, because the irrigation line 216 is not laterally offset in this embodiment, the vertical axis 220 generally passes through the irrigation line 216 and the horn 204. In the illustrated embodiment, the offset angle β enables the irrigation fluid to enter the cavity 210 to the side of the horn 204 (e.g., without directly impinging on the horn 204), which assists in removing more air during priming regardless of orientation of the handpiece 200.

Figure 9:
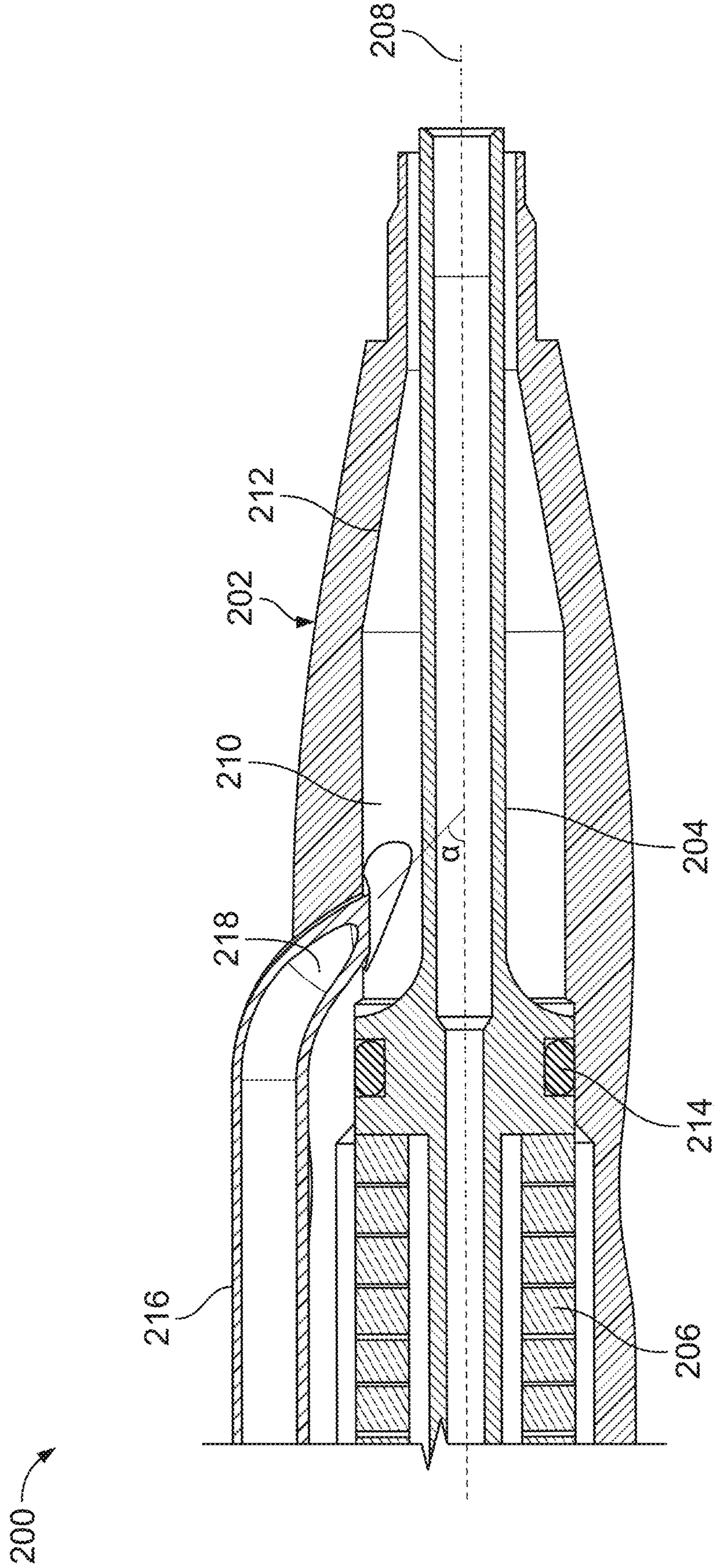
FIG. 9 is a partial side elevation view of the phacoemulsification handpiece of FIG. 6 taken along line 8-8.
Figure 10:
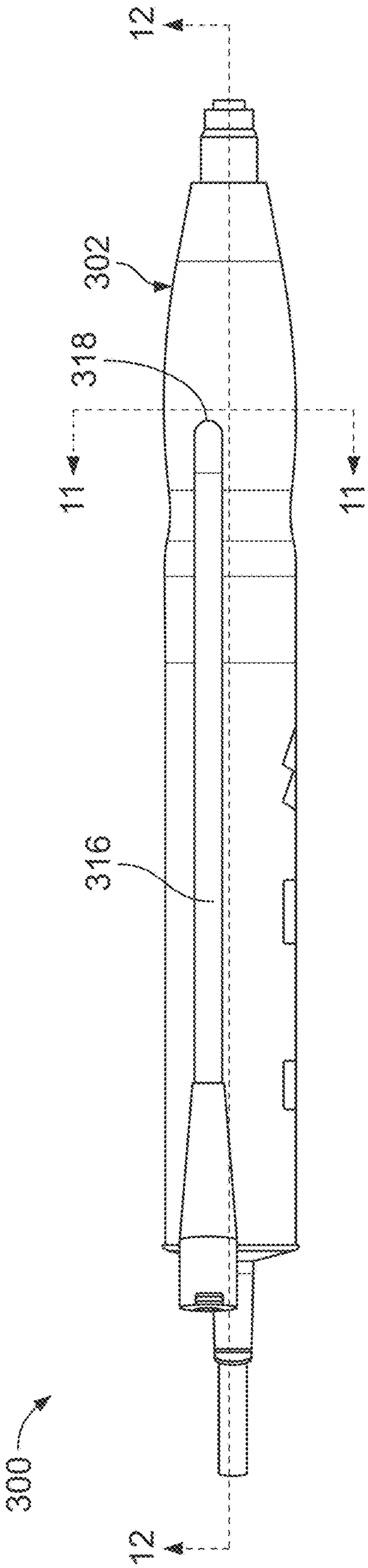
FIG. 10 is a top view of another example embodiment of a phacoemulsification handpiece.
Figure 11B:
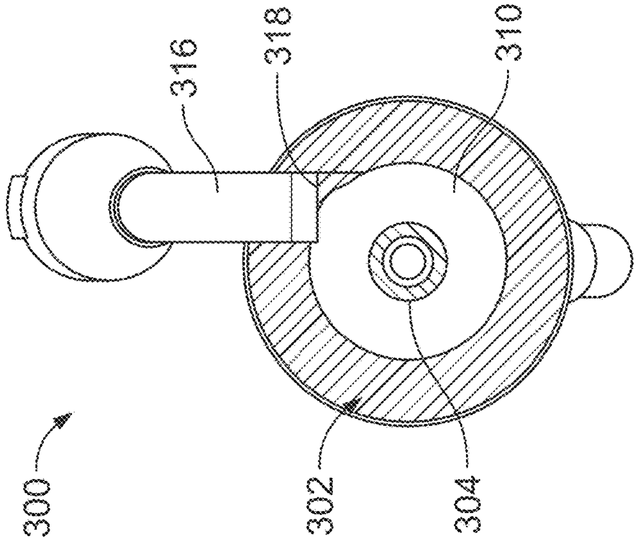
FIG. 11B is a front view of the phacoemulsification handpiece of FIG. 10 taken along line 11-11 in order to illustrate an irrigation port of the phacoemulsification handpiece (e.g., laterally offset from a central axis of the handpiece, etc.)
Figure 11A:
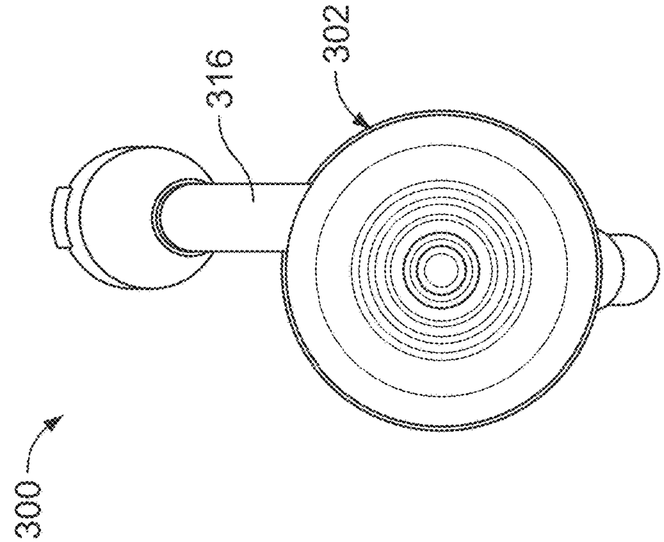
FIG. 11A is a front elevation view of the distal end of the phacoemulsification handpiece of FIG. 10.
Figure 12:
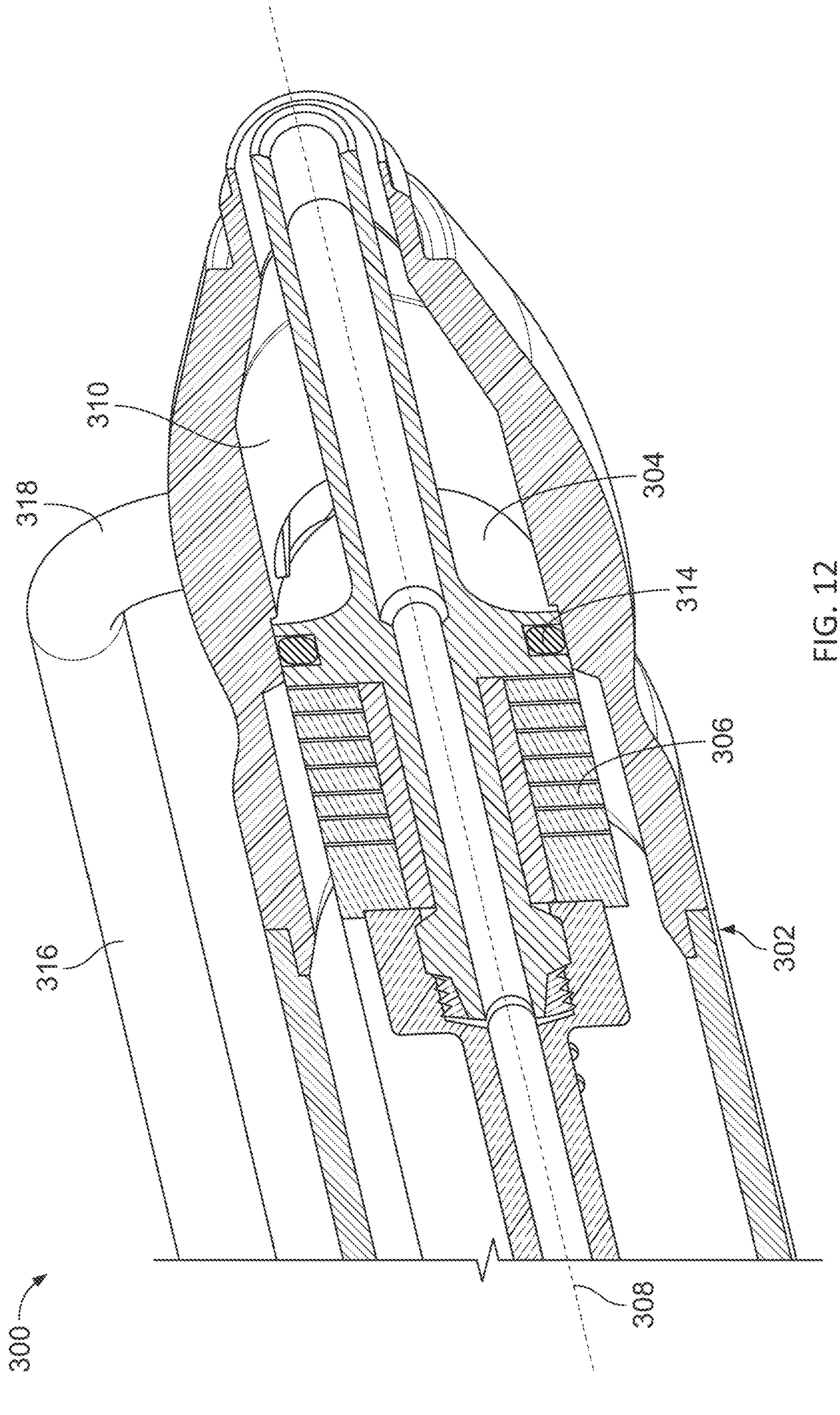
FIG. 12 is a partial side perspective view of the phacoemulsification handpiece of FIG. 10 taken along line 12-12.
Figure 13:
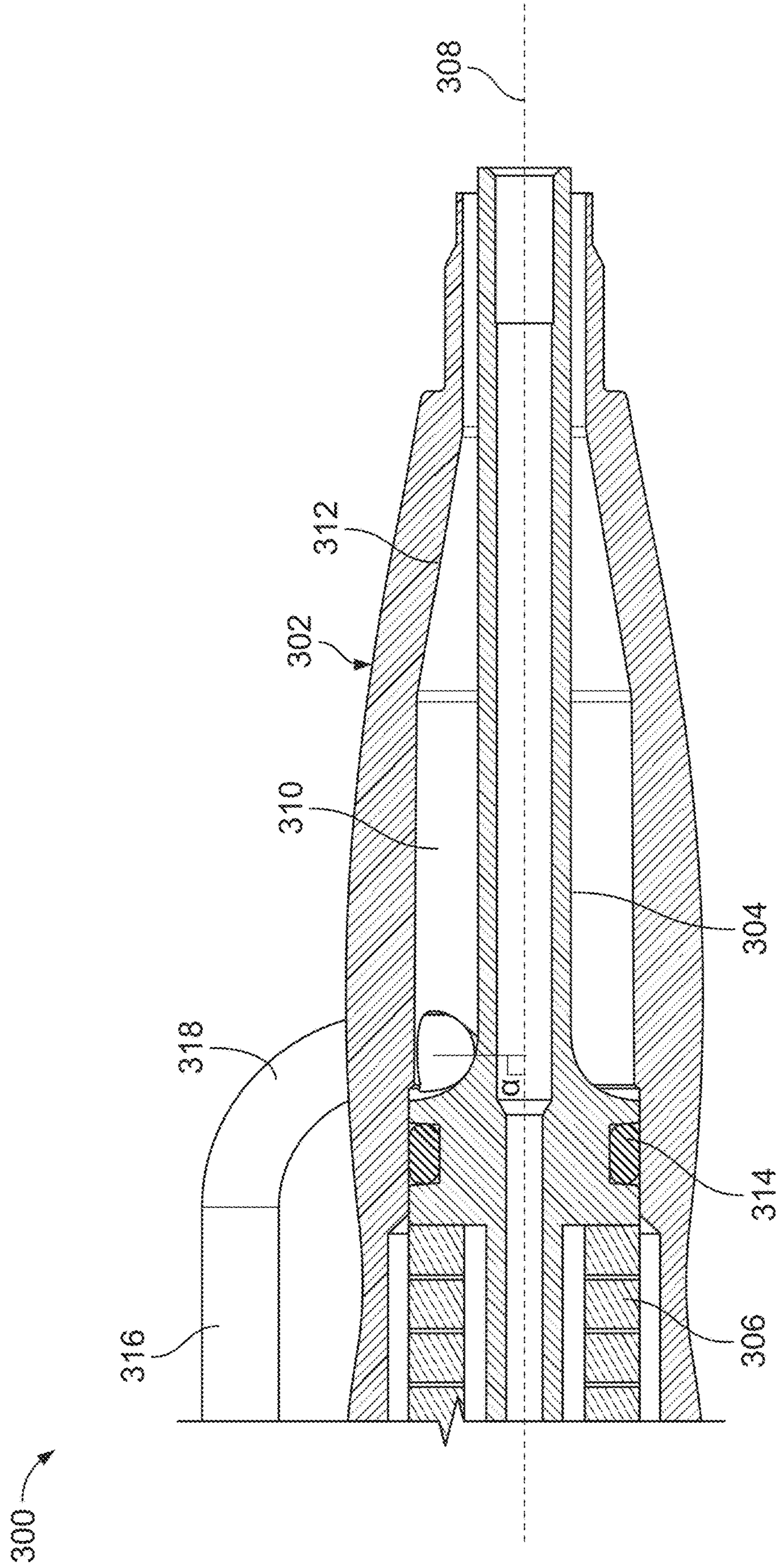
FIG. 13 is a side elevation view of the phacoemulsification handpiece of FIG. 10 taken along line 12-12.
Figure 14:
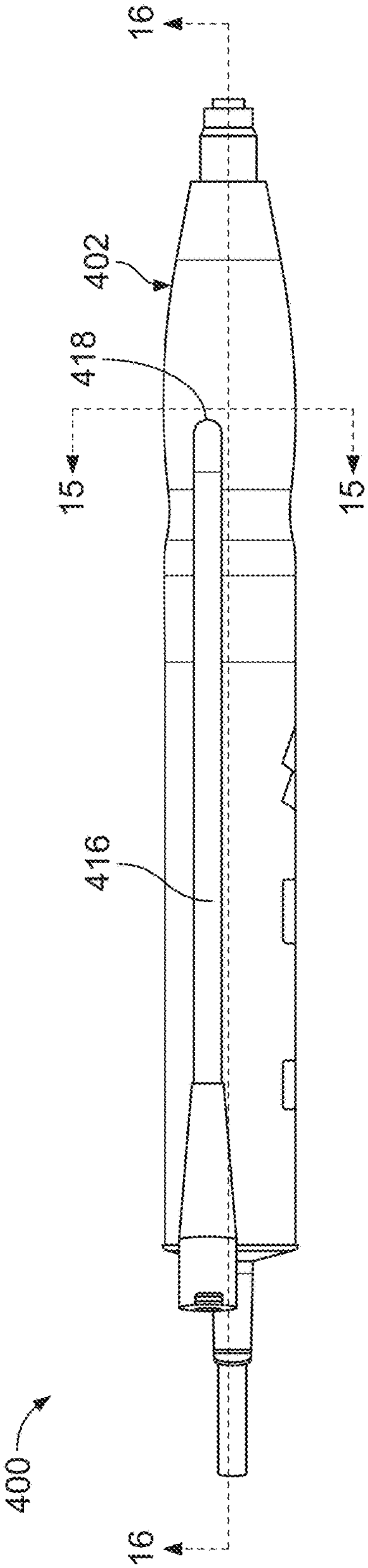
FIG. 14 is a top view of still another example embodiment of a phacoemulsification handpiece.

In addition to being angled with respect to the vertical axis 220 of the handpiece 200 (e.g., by offset angle β), the port 218 is also angled with respect to the central longitudinal axis 208 of the handpiece 200 at an infusion angle α (e.g., similar to port 118). As shown in FIG. 9, the port 218 is angled with respect to the central longitudinal axis 208 such that the irrigation fluid is directed into the cavity 110 at an infusion angle α. In the illustrated embodiment, for example, the infusion angle α of the port 218 is forty-five degrees. However, in other embodiments, the infusion angle α may be greater or lesser (e.g., 30 degrees, 90 degrees, etc.), to optimize the flow of the irrigation fluid into and/or through the cavity 210.

FIGS. 10-13 illustrate another example embodiment of a phacoemulsification handpiece 300 including one or more aspects of the present disclosure. The handpiece 300 of this embodiment is substantially similar to the handpiece 100 previously described and illustrated in FIGS. 2-5. For example, the handpiece 300 includes a housing 302 and a horn 304 (e.g., an ultrasonic transducer horn) that is positioned within a cavity 310 of the housing 302 and is coaxial with a central longitudinal axis 308 of the handpiece 300. The cavity 310 is positioned at a distal end of the housing 302 and is defined, in part, by an inner wall 312 of the housing 302 The handpiece 300 also includes an irrigation line 316 that is coupled to a supply of irrigation fluid (e.g., a saline fluid, BSS, etc.) and a port 318 coupled between the irrigation line 316 and the cavity 310. Similar to the handpiece 100, the irrigation line 316 and the port 318 of the handpiece 300 are laterally offset from the central longitudinal axis 308 to direct the irrigation fluid away from the horn 304 (e.g., to the side of the horn 304, without direct impingement on the horn 304, etc.).

In this embodiment, the port 318 is angled with respect to the central longitudinal axis 308 at an infusion angle α of 90 degrees (e.g., at a right angle with respect to the inner wall 312 of the cavity 310, etc.). Similar to port 118 and port 218, port 318 is positioned at the proximal end of the cavity 310. Angling the port 318 at an infusion angle α of 90 degrees may help ensure that the flow of irrigation fluid within the cavity 310 generally flows from the proximal end of the cavity 310 to the distal end of the cavity 310 (e.g., without backtracking towards the proximal end of the cavity 310). This helps reduce any turbulence in the flow that may occur if the irrigation fluid flows from the port 318 towards the proximal end of the cavity 310 (e.g., when the infusion angle α is less than 90 degrees) and aids evacuation of air from cavity 310.

FIGS. 14-17 illustrate another example embodiment of a phacoemulsification handpiece 400 including one or more aspects of the present disclosure. The handpiece 400 of this embodiment is substantially similar to the handpiece 300 previously described and illustrated in FIGS. 10-13. For example, the handpiece 400 includes a housing 402 and a horn 404 (e.g., an ultrasonic transducer horn) that is positioned within a cavity 410 of the housing 402 and is coaxial with a central longitudinal axis 408 of the handpiece 400. The cavity 410 is positioned at a distal end of the housing 402 and is defined, in part, by an inner wall 412 of the housing 402. The handpiece 400 also includes an irrigation line 416 that is coupled to a supply of irrigation fluid (e.g., a saline fluid, BSS, etc.) and a port 418 coupled between the irrigation line 416 and the cavity 410. Similar to handpiece 100 and handpiece 300, the irrigation line 416 and the port 418 of the handpiece 400 are laterally offset from the central longitudinal axis 408 to direct the irrigation fluid away from the horn 404 (e.g., to the side of the horn 304, without direct impingement on the horn 404, etc.). Similar to the handpiece 300, the port 418 is angled at an infusion angle α of 90 degrees, although in other embodiments, the infusion angle may be different (e.g., less than 90 degrees, 45 degrees, etc.).

In this embodiment, the port 418 partially extends into the cavity 410 and the end 422 of the port 418 is angled (e.g., chamfered). Rather having the end 422 of the port be squared off (e.g., similar to port 118, 218, 318, etc.), the end 422 of the port 418 is angled, such that the portion of the end 422 that is closer to the horn 404 is longer than the portion of the end 422 that is away from the horn 404. Angling (e.g., chamfering) the end 422 of the port 418 in this way further ensures that the irrigation fluid entering the cavity 410 via the port 418 does so without impinging on the horn 404. In particular, the longer portion of the end 422 of the port 418 directs the irrigation fluid away from the horn 404 and towards the inner wall 412 of the cavity 410, such that the irrigation fluid flows generally along (e.g., tangent to) the inner wall of the cavity 410.

Phacoemulsification handpieces of the present disclosure may allow for efficient priming of the handpiece, such that fewer air bubbles are generated by the flow of irrigation fluid (e.g., saline fluid, BSS, etc.) through the handpiece and that more air is removed from the handpiece during priming (e.g., even if the handpiece is not held in the proper orientation during priming (e.g., in a non-vertical or upright position)). The phacoemulsification handpieces of the present disclosure offset the flow of irrigation fluid into the cavity by either laterally offsetting the irrigation port or laterally angling the irrigation port, such that the irrigation fluid does not collide with (e.g., impinge upon) the horn when entering the cavity. Doing so results in a less turbulent flow through the cavity and enables efficient and improved priming of the phacoemulsification handpieces.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Specific dimensions, specific materials, and/or specific shapes disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms “a”, “an” and “the” may be intended to include the plural forms as well, unless the context clearly indicates otherwise. The terms “comprises,” “comprising,” “including,” and “having,” are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being “on”, “engaged to”, “connected to” or “coupled to” another element or layer, it may be directly on, engaged, connected or coupled to the other element or layer, or intervening elements or layers may be present. In contrast, when an element is referred to as being “directly on,” “directly engaged to”, “directly connected to” or “directly coupled to” another element or layer, there may be no intervening elements or layers present. Other words used to describe the relationship between elements should be interpreted in a like fashion (e.g., “between” versus “directly between,” “adjacent” versus “directly adjacent,” etc.). As used herein, the term “and/or” as well as the phrase “at least one of” includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as “first,” “second,” and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as “inner,” “outer,” “beneath”, “below”, “lower”, “above”, “upper”, “lower” and the like, may be used herein for ease of description to describe one element or feature’s relationship to another element(s) or feature(s) as illustrated in the figures. Spatially relative terms may be intended to encompass different orientations of the device in use or operation in addition to the orientation depicted in the figures. For example, if the device in the figures is turned over, elements described as “below” or “beneath” other elements or features would then be oriented “above” the other elements or features. Thus, the example term “below” can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the present disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the present disclosure, and all such modifications are intended to be included within the scope of the present disclosure.

What is claimed is:

1. A phacoemulsification handpiece for ophthalmic surgery, the phacoemulsification handpiece comprising:

a housing including a cavity positioned at a distal end of the housing;

a horn positioned at least partially within the cavity;

an irrigation line coupled to the housing;

a port coupled between the irrigation line and the cavity, wherein the port is configured to direct fluid into the cavity to a side of the horn with respect to a central longitudinal axis to facilitate a flow of irrigation fluid around the horn and mitigate generation of air bubbles.

2. The phacoemulsification handpiece of claim 1, wherein the port and the irrigation line are laterally offset from the horn.

3. The phacoemulsification handpiece of claim 1, wherein the irrigation line is aligned with the central longitudinal axis; and wherein an offset angle of the port with respect to the central longitudinal axis is non-zero.

4. The phacoemulsification handpiece of claim 1, wherein the port is positioned at a proximal end of the cavity and an infusion angle of the port is ninety degrees with respect to an inner wall of the cavity.

5. The phacoemulsification handpiece of claim 1, wherein the end of the port is beveled.

* * * * *